United States Patent [19]

Morales et al.

[11] Patent Number: 5,407,927
[45] Date of Patent: Apr. 18, 1995

[54] TREATMENT OF MILD DEPRESSION AND RESTORATION OF IGF-I LEVELS IN AGING BY DEHYDROEPIANDROSTERONE

[75] Inventors: Arlene J. Morales, San Diego; Samuel S. C. Yen, La Jolla, both of Calif.

[73] Assignee: The Regents of the University of California, Oakland, Calif.

[21] Appl. No.: 49,729

[22] Filed: Apr. 16, 1993

[51] Int. Cl.$^6$ .................. A61K 31/56; A61K 31/595
[52] U.S. Cl. .................... 514/177; 514/170; 514/178; 514/182
[58] Field of Search ............. 514/120, 177, 182, 178

[56] References Cited

U.S. PATENT DOCUMENTS

| | | | |
|---|---|---|---|
| 4,628,052 | 12/1986 | Peat | 514/171 |
| 4,666,898 | 5/1987 | Coleman et al. | 514/177 |
| 4,812,447 | 3/1989 | Roberts | 514/170 |
| 4,956,355 | 9/1990 | Prendergast | 514/178 |
| 5,077,284 | 12/1991 | Loria et al. | 514/171 |
| 5,084,445 | 1/1992 | Chu et al. | 514/49 |
| 5,206,008 | 4/1993 | Loria | 424/45 |
| 5,277,907 | 1/1994 | Loria | 424/93 |

OTHER PUBLICATIONS

Morales, A. J., et al., "Endocrine, Metabolic, and Quality of Life Effects of Three Months of Nightly Administration of Dehydroepiandrosterone (DHEA) to Adults Age 40–65," The Endocrine Society, 74th Annual Mtg., Abstract 841, pp. 262 (Jun. 24–27, 1992).

Morales, A. J., et al., "Serum Dehydroepiandrosterone (DHEA) and DHEA Sulfate (DS) Levels after Three Months of Administration of 50 Mg. Oral DHEA: Gender Difference," Society for Gynecologic Investigation, 39th Annual Mtg., Abstract 371, p. 294 (Mar. 18–21, 1992).

Clemmons, D. R., "Editorial: Role of Insulin–Like Growth Factor-1 in Reversing Catabolism," *J. Clin. Endocrinology and Metabolism*, 75(5):1183–1185 (1992).

Düsterberg, B., et al., "Plasma Levels of Dehydroepiandrosterone and 17β-Estradiol after Intramuscular Administration of Gynodian-Depot ® in 3 Women," *Hormone Res.*, 17:84–89 (1983).

*Primary Examiner*—Raymond Henley, III
*Assistant Examiner*—T. J. Criares
*Attorney, Agent, or Firm*—Townsend and Townsend Khourie and Crew

[57] ABSTRACT

This invention relates to the treatment of mild depression in an aging patient population. The invention specifically relates to daily treatment with dehydroepiandrosterone to increase insulin-like growth factor-I serum levels and increase psychological well-being in these patients.

18 Claims, 5 Drawing Sheets

TREATMENT OF MILD DEPRESSION AND RESTORATION OF IGF-I LEVELS IN AGING BY DEHYDROEPIANDROSTERONE

This invention was made with Government support under Grant No. PR-00827 awarded by the National Institutes of Health. The Government has certain rights in this invention.

BACKGROUND OF THE INVENTION

This invention relates to the treatment of mild depression in an aging patient population. The invention specifically relates to daily treatment with dehydroepiandrosterone to increase insulin-like growth factor-I serum levels and increase psychological well-being in these patients.

SUMMARY OF THE INVENTION

This invention provides for a method of increasing endogenous levels of insulin-like growth factor-I (IGF-I) in mature humans by treatment with daily doses of 15–150 mg of dehydroepiandrosterone (DHEA). Preferentially the treated humans are from 40–80 years of age, and more preferentially from 50–70 years of age. The dose of DHEA is preferentially from 15–100 mg, and more preferentially from 40–100 mg. The method of administration of DHEA is either oral or sublingual, and the time period of daily administration exceeds 3 months.

This invention also provides for a method of treating mature humans with mild depression by treatment with daily doses of DHEA. Preferentially the humans are from 40–80 years of age and more preferentially from 50–70 years of age. The dose of DHEA is preferentially between 15–150 mg, and more preferentially between 40 and 100 mg. The method of administration of DHEA is either oral or sublingual, and the time period of daily administration exceeds 3 months.

This invention further provides for a method of increasing well being using the therapeutic parameters described above.

BRIEF DESCRIPTION OF THE FIGURES

FIG. 4: (a) Serum levels of IGF-I and IGF BP-I in men at baseline, 3 months of DHEA (50 mg) and 3 months of placebo treatments. (b) Serum levels of IGF-I and IGF BP-I in women at baseline, 3 months of DHEA (50 mg) and 3 months of placebo.

DESCRIPTION OF THE PREFERRED EMBODIMENT

Introduction

This invention provides for a novel use of DHEA which is the treatment of aging patients with mild depression. Mild depression is common in the aging population and administration of DHEA can therefore result in major improvement in quality of life for many such patients. DHEA is a naturally occurring hormone and its blood levels decrease with age. This invention treats defined patients with physiological doses of DHEA given orally or sublingually which results in an increase in (IGF-I) blood levels and in increased feelings of psychological well-being in these patients.

DHEA pharmacology

DHEA is an androgenic steroid produced by the adrenal gland. DHEA and its sulfated form, DHEAS, are the major androgens secreted by the adrenal gland. Circulating levels of DHEA and DHEAS peak during the third decade of life and thereafter progressively decline to very low levels in senescence. Barrett-Conner, E., et al., 1986, N. Engl. J. Med. 315:1519.)

DHEA has been given in pharmacological doses in clinical trials. There are also pharmacological preparations of DHEA that are used experimentally. For example, DHEA is included with estradiol in a preparation called Gynodian-Depot which is administered intramuscularly for treatment of psychological and somatic symptoms associated with the female menopause (Dusterberg, B., et al., 1983, Hormone Res., 17:84-89). DHEA has also been used experimentally in treatment of degenerative diseases of the central nervous system (U.S. Pat. No. 4812447), and in treatment of arthritis and other autoimmune diseases (U.S. Pat. No. 4628052) and in treatment of immune system disorders (U.S. Pat. No. 5,077,284).

The above studies have been carried out at pharmacological levels of DHEA administration which generally exceed either the single dose level or are carried for less time than specified by this invention. In this invention lower levels of DHEA are administered orally. Fifty to 100 mg of DHEA are administered orally or sublingually on a daily basis. When administered to adults from 40–80 years old, this dosage results in blood levels of DHEA that are in the physiological range for younger adults (See FIG. 1).

Patient Selection

Both male and female patients from 40–80 years old with mild depression are selected. More preferentially patients from 50–70 years old also with mild depression are selected. Patients are otherwise free of mental illness.

Administration of DHEA

DHEA is administered orally in capsule or in tablet form or will be given sublingually as a solution or suspension.

Pharmaceutical compositions of the invention are suitable for use in a variety of drug delivery systems. For a brief review of present methods for drug delivery, see, Langer, Science 249:1527-1533 (1990), which is incorporated herein by reference. Methods for preparing administrable compounds will be known or apparent to those skilled in the art and are described in more detail in, for example, Remington's *Pharmaceutical Science*, 17th ed., Mack Publishing Company, Easton, PA (1985), which is incorporated herein by reference, and which is hereinafter referred to as "Remington."

For solid compositions, conventional nontoxic solid carriers may be used which include, for example, pharmaceutical grades of mannitol, lactose, starch, magnesium stearate, sodium saccharine, talcum, cellose, glucose, sucrose, magnesium, carbonate, and the like. For oral administration, a pharmaceutically acceptable nontoxic composition is formed by incorporating any of the normally employed excipients, such as those carriers previously listed.

Oral solid dosage forms are preferentially compressed tablets or capsules. Compressed tablets may contain any of the excipients described above which are diluents to increase the bulk of the of the DHEA so that production of a compressed tablet of practical size is possible. Binders, which are agents which impart cohesive qualities to powdered materials are also necessary. Starch, gelatin, sugars such as lactose or dextrose, and natural and synthetic gums are used. Disintegrants are necessary in the tablets to facilitate breakup of the tablet. Disintegrants include starches, clays, celluloses, algins, gums and cross-linked polymers. Lastly small amounts of materials known as lubricants and glidants are included in the tablets to prevent adhesion to the tablet material to surfaces in the manufacturing process and to improve the flow characteristics of the powder material during manufacture. Colloidal silicon dioxide is most commonly used as a glidant and compounds such as talc or stearic acids are most commonly used as lubricants. Procedures for the production and manufacture of compressed tablets are well known by those skilled in the art (See Remington).

Capsules are solid dosage forms using preferentially either a hard or soft gelatin shell as a container for the mixture of DHEA and inert ingredients. Procedures for production and manufacture of hard gelatin and soft elastic capsules are well known in the art (See Remington).

DHEA is administered sublingually preferentially as an aqueous solution or a suspension. Suspensions are prepared by use of a suspending agent, which is added either as a dry powder mixed with powdered DHEA prior to suspension, or which is added after the DHEA particles are wetted in an aqueous mixture containing a surface active agent. Methods for production and manufacture of aqueous solutions and suspensions are well known in the art (See Remington).

DHEA is administered preferentially in dosages of 40 to 100 mg, which in a 70 kg person is equivalent to a dosage range of 0.57 mg/kg to 1.43 mg/kg of body weight body weight. DHEA is administered preferentially for a period of time until the patient has fully responded with an increase in psychological well-being and his physician orders discontinuation of the treatment.

Determining patient response

Blood specimens are drawn from patients immediately prior to the onset of DHEA administration and preferentially at 30 days after the beginning of treatment and at periodic intervals thereafter determined by the treating physician. Serum IGF-I and IGF BP-I levels are determined by immunoassay on these blood specimens. There are a variety of immunoassay methods available for determination of IGF-I and IGF BP-I which are reported in the literature and which are known to those of skill in the art. (Breier, B.H., et al., *J. of Endocrinol.*, 1991, 128:347-357 and Pekonen, F. et al. *J. Immunoassay*, 1989, 10:325-337.

Significant elevation in IGF-I levels above pretreatment levels indicates a physiological response to the DHEA. Comparison of IGFBP-I levels pre- and post-treatment aids in the interpretation of the IGF-I levels since the free (unbound) IGF-I is the physiologically important species. For example, a decrease in IGF BP-I levels would potentiate any increases in IGF-I, since the levels of free IGF-I would increase.

Determination of psychological response is determined by administration of tests for psychological well-being. Preferentially the General Well Being Scale and the Bush's Quality of Well-Being Scale are administered to the patient to determine psychological response. (See Kaplan, R.M. et al., 1982, Health Psychol. 1: 61-80; Dupuy, HJ, 1974, Nat. Conf. M Ed., Alcoholism, Drug Abuse & Mental Health Prog., Wash D.C.; Kaplan, R.M., et al., 1976, Health Serv. Res. 11: 478-507; Patrick, D., et al., 1973, Health Serv. Res. 8: 228-245; Anderson J.P. et al., 1989, Med. Care 27: 1076-1084.)

Statistically significant increases in the scores of these well-being tests are used as a measure of an improvement in psychological well-being in these patients. Patients are also evaluated for the presence of symptoms of depression by means of psychiatric evaluations by medical personnel to determine patient responsiveness and the need for continuation of DHEA treatment.

Definitions

The term "APO-Ai" refers to apolipoprotein A1.

The term "APO-A2" refers to apolipoprotein A2.

The term "BMI" means body mass index which is body weight (kg)/height ($m^2$).

The term "DHEA" means dehydroepiandrosterone.

The term "DHEAS" means dehydroepiandrosterone-sulfate.

The term "HDL" means high density lipoprotein.

The term "IGF-I" refers to insulin-like growth factor one.

The term "IGF BP-I" refers to insulin-like growth factor binding protein one.

The term "LDL" means low density lipoprotein.

The term "mild depression" refers to affective disorders defined in the DSM-IIIR Manual including cyclothymic disorder (DSM-IIIR 301.13), dysthymic disorder (DSM-IIIR 300.40) and depressive disorder not otherwise specified (DSM-IIIR/311.00). (See *Diagnostic and Statistical Manual of Mental Disorders, DSM-IIIR*, Third Edition Revised, 1987, American Psychiatric Association, Washington, D.C., hereinafter referred to as DSM-IIIR.) These disorders are all chronic mood disturbances in which major depressive episodes and major depressive illnesses have been ruled out. The essential feature is depressed mood or loss of interest in usual activities and pastimes, with associated symptoms, but not of sufficient severity or duration to meet the criteria for a major depressive episode. The depressed mood may have associated symptoms of loss of appetite, or either insomnia or hypersomnia. Difficulty in concentrating, and slowed thinking may be present, and the patient often experiences feelings of worthlessness or inadequacy. (See DSM-IIIR.) The term "TG" refers to triglycerides.

The following examples are provided by way of illustration only and not by way of limitation. Those of skill will readily recognize a variety of noncritical parameters which could be changed or modified to yield essentially similar results.

EXAMPLES

EXAMPLE ONE: Treatment of a sixty year old male with oral DHEA

A sixty year old male with mild depression is selected for treatment. Major depressive illness has been ruled out, but the patient has symptoms of depressed mood or loss of interest in all or most usual pastimes and activities. The patient may have a diagnosis of cyclothymic disorder, dysthymic disorder or depressive disorder not otherwise specified. (See DSM-IIIR.) The patient is otherwise physically and psychologically healthy.

The patient is treated with 50 mg of DHEA administered orally on a daily basis for a period of 30 days. Blood specimens are drawn from the patient at day 0, just prior to start of treatment, and at day 30, after the last dose of DHEA has been given. Serum IGF-I and IGF BP-I are measured by standard immunoassays.

The patient is tested for well-being before and after the administration of DHEA. Two well-known tests for psychological well-being are used. The General Well Being Scale is a self-administered questionnaire with a reliability coefficient of 0.745. The interviewer administered Bush's Quality of Well-Being Scale is also administered. (See Kaplan, et al., 1982; Dupuy, 1974; Kaplan, et al., 1976; Patrick, et al., 1973; and Anderson, et al., 1989.)

EXAMPLE TWO: Treatment of a sixty year old female with oral DHEA

A sixty year old female patient with mild symptoms of depression is selected. The patient meets the diagnostic criteria described in example 1 for depression and is otherwise physically and psychologically healthy.

The patient is treated by administration of oral DHEA for a period of 30 days as described in example 1. Serum specimens are collected and IGF-I and IGF BP-I are measured as described in example 1. Lastly, well-being tests are administered before and after DHEA treatment as described in example 1.

EXAMPLE THREE: Measurements of metabolism and well-being in 30 patients treated with oral DHEA a) Subject Selection and Study Design Seventeen women and 13 men ages 40–70 in good medical health were enrolled in a clinical trial of DHEA replacement of 6 months duration. The trial was structured as a double-blind randomized placebo-controlled crossover study. No side effects were reported from this trial. Safety parameters (physical exams, hematology, chemistry) were obtained and were all within normal limits. These subjects were seen monthly and received 50 mg DHEA orally, nightly for 3 months and placebo for 3 months.

b) Steroid Hormone Levels

Blood specimens were drawn from all subjects in the study at baseline (time 0) and at 2 weeks and 12 weeks after DHEA administration, and at 2 weeks after DHEA administration was discontinued. DHEA, DHEAS, androstenedione, testosterone, dihydrotestosterone, and the sex hormone binding globulin were all measured by immunoassay as described by Anderson, D.C., et al. Steroid, 1976, 28:179.

Figure 1:
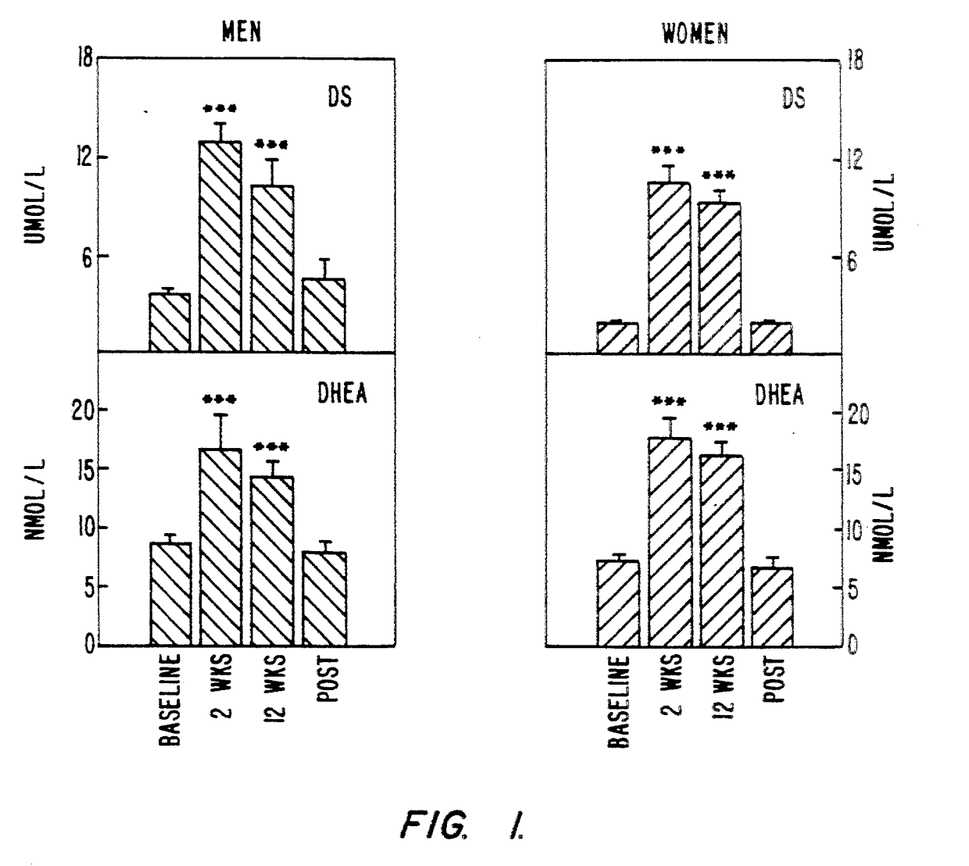
FIG. 1: DHEAS and DHEA serum levels in men and women at baseline, 2 and 12 weeks of DHEA (50 mg) administration and 2 weeks after discontinuation. The horizontal solid line represents mean level during the second decade of life.
Figure 2:
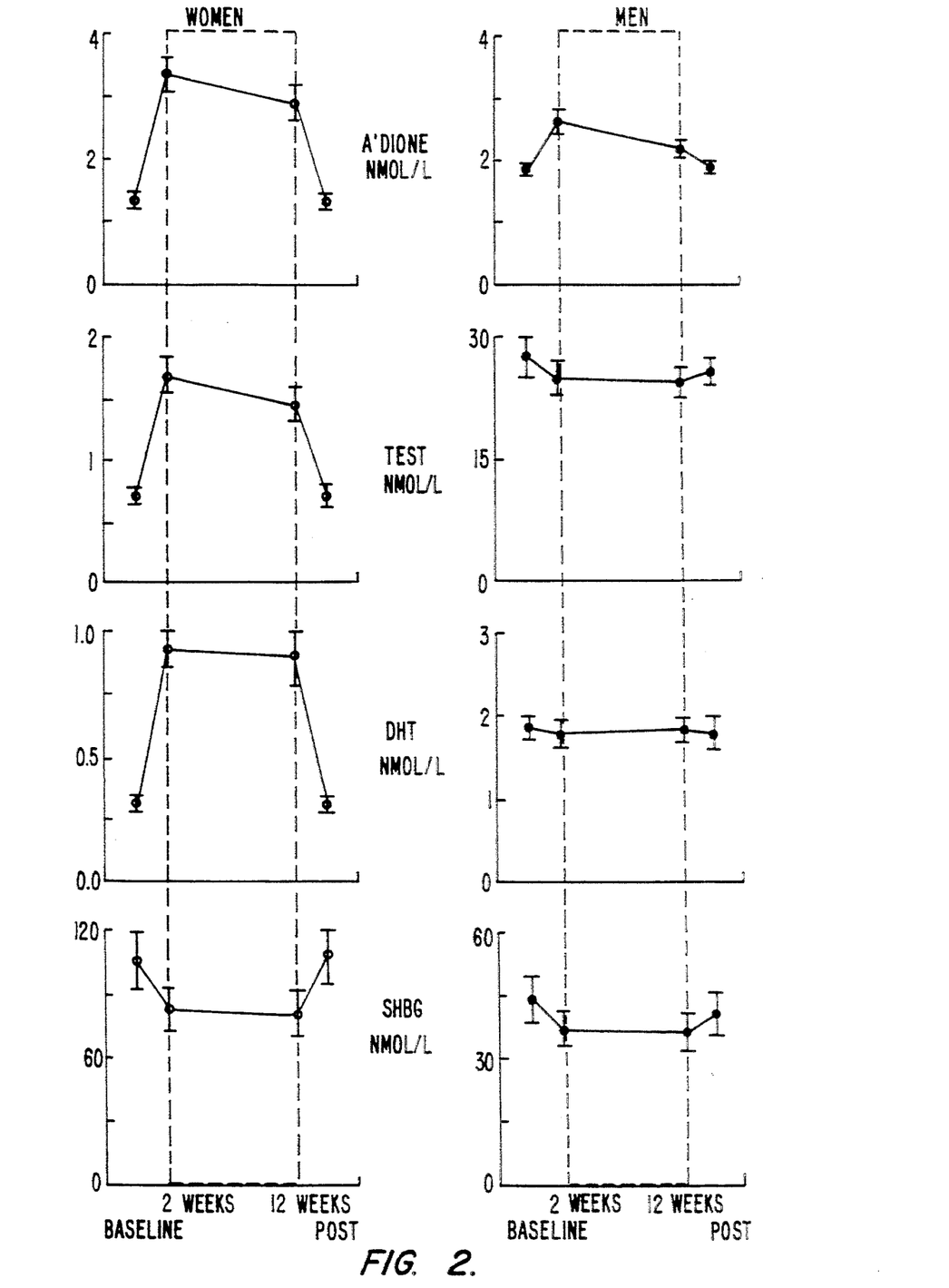
FIG. 2: Hormonal levels during DHEA (50 mg) therapy (represented by stippled area) in men and women. ADIONE (androstenedione); TEST (testosterone); DHT(dihydrotestosterone); SHBG(sex-hormone binding globulin). The shaded area represents the duration of DHEA treatment.

DHEA and DHEAS serum levels are shown in FIG. 1. DHEAS levels in men and women rose to those levels seen in the second decade of life within 2 weeks of administration. These levels were maintained throughout the three month trial and returned to baseline within 2 weeks after discontinuing the DHEA. Serum levels of testosterone, androstenedione, and dihydrotestosterone, as well as the sex-hormone binding globulin are shown in FIG. 2. Evaluation of this data revealed that women had a doubling of their androgen levels (testosterone, androstenedione, dihydrotestosterone) while men demonstrated no changes in any androgens, particularly dihydrotestosterone and estrogens. Sex-hormone binding globulin, a major carrier protein of androgens and estrogens, revealed a trend of decline but this decline was not statistically significant.

c) Body composition and glucose metabolism

Insulin sensitivity and glucose effectiveness were measured by euglycemic hyperinsulinemic clamp (Bergman, R.N. *J. Clin. Invest.*, 1987, 79:790-800) and rapid intravenous glucose tolerance test (Bergman, R.N., et al. *Amer. J. Physiol.*, 1979, 236:667-677) and % body fat as measured by bioelectric impedance (Lukaski, H. *Amer. J. Nutrition*, 1987, 46:537) were measured on all patients after DHEA of placebo treatment. The glucose disposal rate was also measured using Bergman, 1987 (supra). The results of these measurements are shown in Table 1.

TABLE 1
EFFECTS OF REPLACEMENT DOSE OF DHEA
ON BODY COMPOSITION AND GLUCOSE METABOLISM
(MEAN ± STANDARD ERROR)

|  | WOMEN | | MEN | |
| --- | --- | --- | --- | --- |
|  | PLACEBO | DHEA | PLACEBO | DHEA |
| % FAT | 31.0 ± 1.0 | 31.3 ± 1.0 | 22.1 ± 1.2 | 21.9 ± 1.3 |
| BMI (kg/m$^2$) | 24.8 ± 0.7 | 24.7 ± 0.7 | 27.3 ± 0.8 | 27.0 ± 0.7 |
| INSULIN SENSITIVITY ($\times 10^{-4}$ min$^{-1}$ uU$^{-1}$ ml) |  | 2.90 ± 0.4 | 2.89 ± 0.6 | 3.69 ± 0.5 |
| GLUCOSE EFFECTIVENESS (min$^{-1}$) | 0.018 ± 0.001 | 0.024 ± 0.002 | 0.022 ± 0.002 | 0.019 ± 0.001 |
| GLUCOSE DISPOSAL RATE (mg/kg/min) |  |  | 8.410 ± 1.26 | 7.64 ± 0.056 | d) Cholesterol, Lipids and Lipoproteins

Serum cholesterol, triglycerides, apolipoproteins A1 and B, and the HDL and LDL lipoproteins were measured on all serum specimens. Cholesterol, triglycerides, HDL and LDL were measured by standard enzymatic methods. (Allain, C.A., et al., *Clin. Chem.* 1974, 20:470.) Apolipoproteins were measured by immunoassay methods. Immunoassay methods for measurement of apolipoproteins are described in the literature. (Frankel, A.L., *Steroids,* 1975, 25:73.) The results of these measurements are shown in Table 2. Only a small reduction in HDL levels were seen in women. All other lipid or lipoprotein levels were unchanged by the DHEA administration.

TABLE 2

EFFECT OF DHEA (50 MG) × 3 MONTHS ON LIPIDS AND APOLIPOPROTEINS (MEAN ± STANDARD ERROR)

|  | WOMEN | MEN |
|---|---|---|
| CHOLESTEROL | | |
| PLACEBO | 223.7 ± 5.8 | 204.3 ± 7.9 |
| DHEA | 218.3 ± 6.9 | 209.9 ± 9.4 |
| HDL | | |
| PLACEBO | 68.7 ± 2.6 | 45.4 ± 2.5 |
| DHEA | 63.4 ± 2.7 | 44.8 ± 1.7 |
| LDL | | |
| PLACEBO | 141.2 ± 6.2 | 140.4 ± 6.9 |
| DHEA | 136.0 ± 4.9 | 147.5 ± 8.5 |
| APO A1 | | |
| PLACEBO | 222.8 ± 8.1 | 165.4 ± 5.3 |
| DHEA | 213.7 ± 8.1 | 167.4 ± 6.1 |
| APO B | | |
| PLACEBO | 137.2 ± 5.8 | 143.0 ± 7.3 |
| DHEA | 137.4 ± 5.9 | 149.8 ± 8.5 |
| TG | | |
| PLACEBO | 102.5 ± 9.2 | 114.5 ± 13.5 |
| DHEA | 94.2 ± 7.4 | 107.7 ± 10.5 | e) Well Being and Libido

Sense of well-being or mood-elevating effect was reported in response to a question: "Have you noted any effect, good or bad during this treatment?" Responses ranged from "sleeping better" "better ability to handle stress" "more relaxed", "easier time falling asleep", "more energy" and "better moods".

Figure 3A:
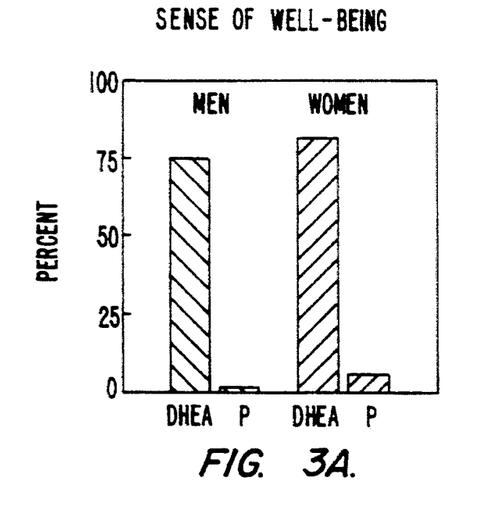
FIG. 3: Sense of Well-being and Libido in men and women on 3 months of DHEA (50 mg) and placebo.
Figure 3B:
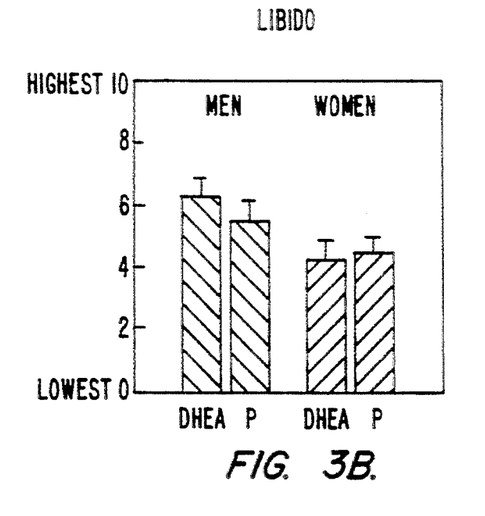
Figure 4A:
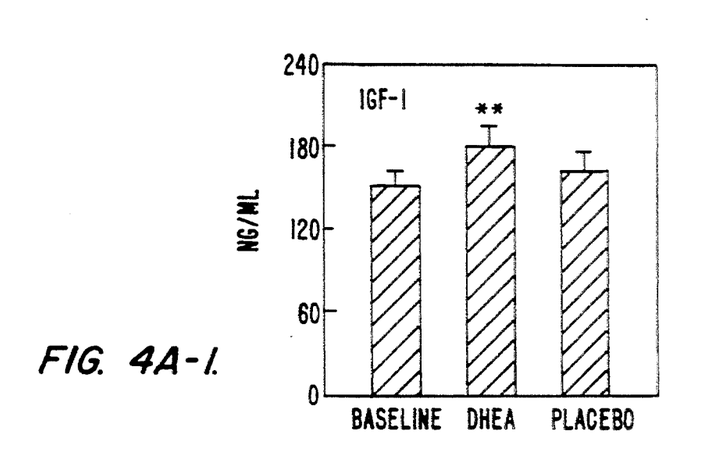
Figure 4A:
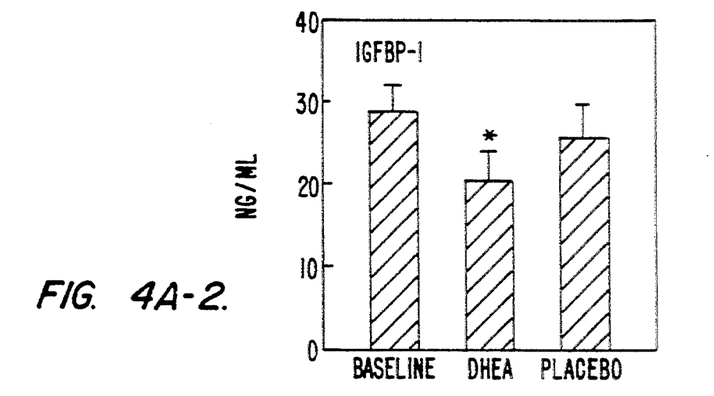
Figure 4B:
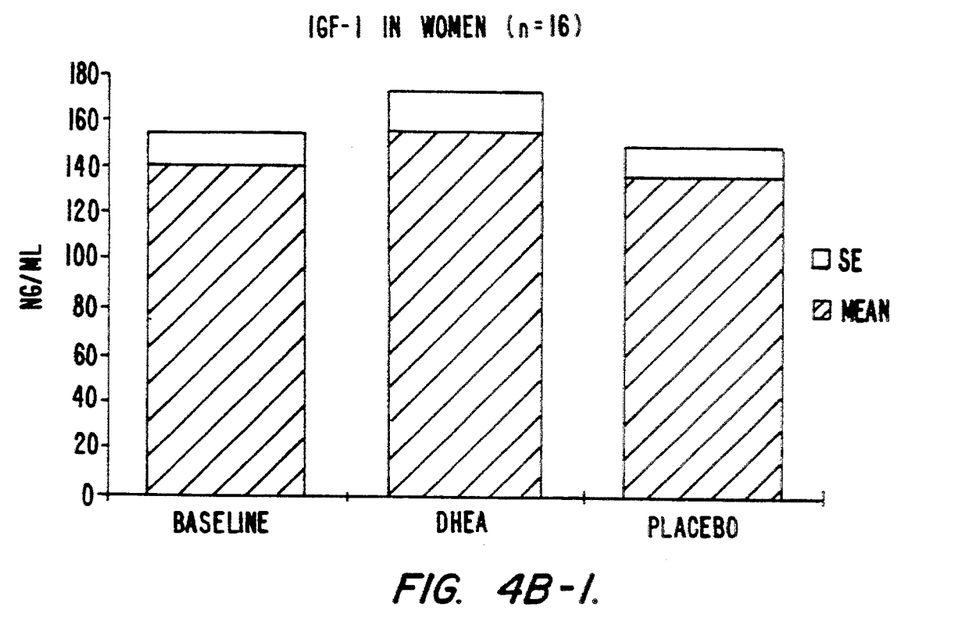
Figure 4B:
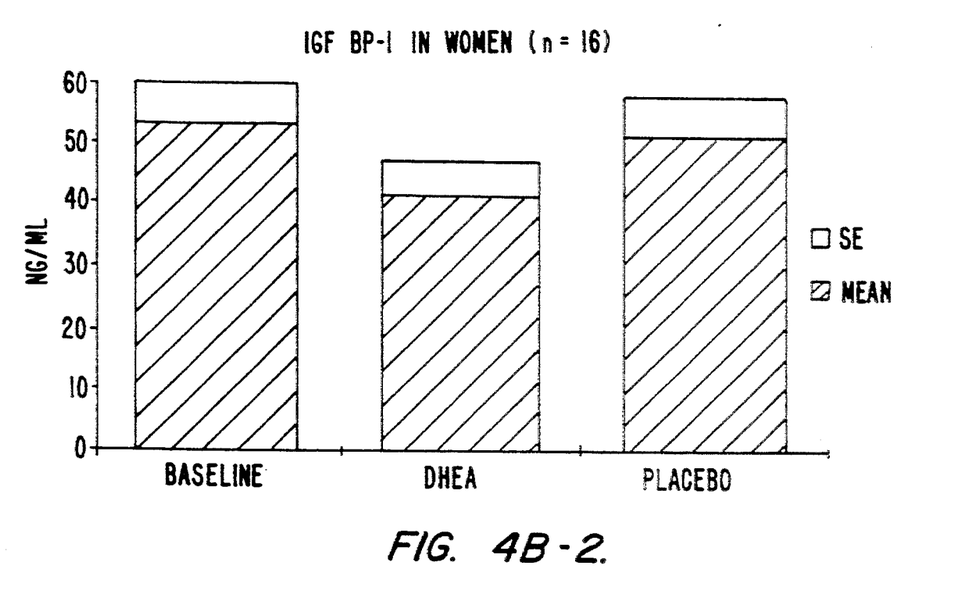
Figure 5A:
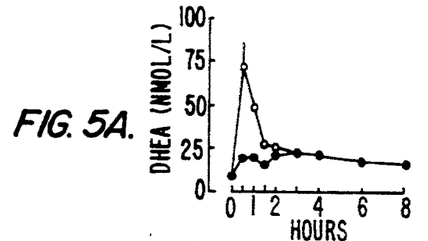
FIG. 5: Hormonal levels in men and women after oral 50 mg DHEA (●) and sublingual 50 mg. DHEA (○).
Figure 5B:
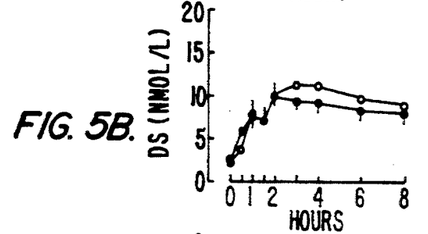
Figure 5C:
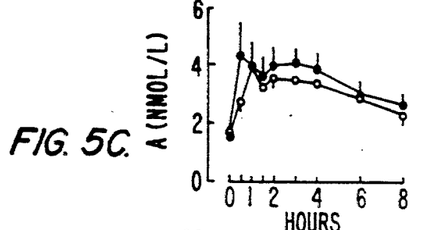
Figure 5D:
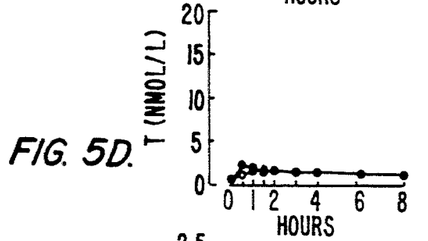
Figure 5E:
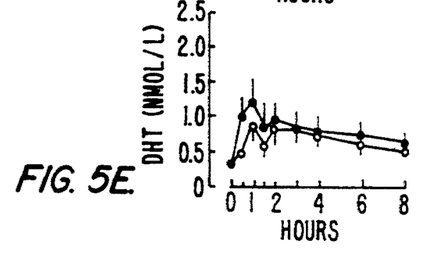
Figure 5F:
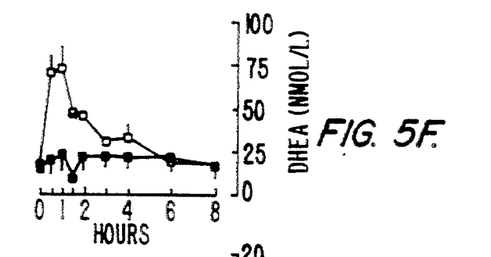
Figure 5G:
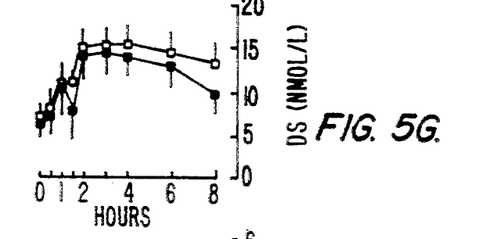
Figure 5H:
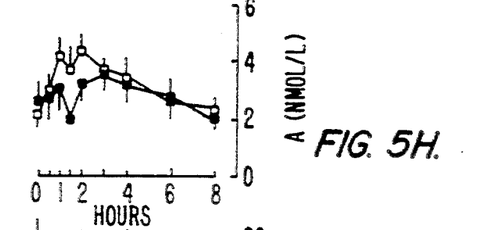
Figure 5I:
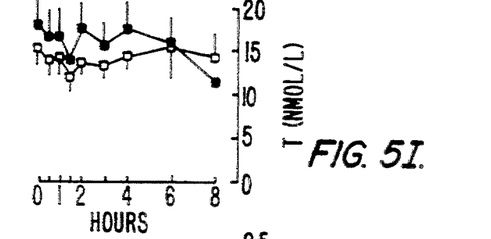
Figure 5J:
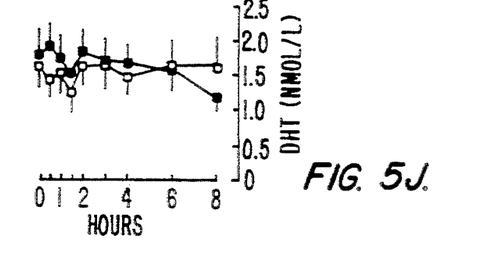

Libido was self-reported by the patients and scored on a visual analog scale. Subjects were evaluated at the end at the 3 month period of DHEA or placebo treatment. Although a significant gender difference was noted in self-reported libido (on a visual analog scale), no difference was seen while subjects were on DHEA. An impressive mood-elevating effect was noted in retrospect by the majority of both men and women. See FIG. 3.

f) Insulin-like growth factors

Insulin-like growth factor I and insulin-like growth factor binding protein I were measured in serum specimens by immunoassay as described previously.

The results from the measurements made on serum specimens from men and women are shown in FIG. 4. Most interesting, both groups showed a statistically significant elevation of insulin-like growth factor I (IGF-I) and a decrease in insulin-like binding protein I (IGF BP-I). This leads to an overall increase in free IGF-I, an important trophic factor that is known to decrease in aged men and women. In men IGF BP-I decreased 12% and IGF-I increased 10%, while in women IGF BP-I decreased 22% and IGF-I increased 12%.

g) Pharmacokinetics

A pharmacokinetic study comparing oral and sublingual administration of DHEA was performed on the men and women subjects. DHEA, DHEAS, androstenedione, testosterone and dihydrotestosterone were measured by the immunoassay methods described above on serum specimens drawn at 30 minutes, 1 hour, 2 hours, 4 hours, 5 hours and 8 hours after dose administration. Both routes or administration yielded similar levels of DHEA, DHEAS and androgens at 8 hours in both men and women. Peak levels of DHEA were achieved within 30 minutes with the sublingual route and 3 hours with the oral route. Therefore, the DHEA is absorbed most rapidly sublingually. The results are shown in FIG. 5.

What is claimed is:

1. A method for increasing endogenous levels of IGF-I in mature humans, said method comprising administration of DHEA in a daily amount of between 15 and 150 milligrams to a human between the ages of 40 and 80 years in need of treatment for mild depression, wherein the administration continues for a period in excess of seven days.

2. A method of claim 1 wherein the mode of administration is oral.

3. A method of claim 1 wherein the mode of administration is sublingual.

4. A method of claim 1 wherein the human is a man.

5. A method of claim 1 wherein the human is a woman.

6. A method of claim 1 wherein the daily amount is between 40 and 100 milligrams.

7. A method of claim 1 wherein the human is between 50 and 70 years of age.

8. A method of claim 1 wherein the daily administration is between one month and six months.

9. A method of claim 1 wherein the daily administration exceeds one month.

10. A method for treating mild depression in mature humans said method comprising administration of DHEA in a daily amount of between 15 and 150 milligrams to a human between the ages of 40 and 80 years.

11. A method of claim 10 wherein the mode of administration is oral.

12. A method of claim 10 wherein the mode of administration is sublingual.

13. A method of claim 10 wherein the human is a man.

14. A method of claim 10 wherein the human is a woman.

15. A method of claim 10 wherein the daily amount is between 40 and 100 milligrams.

16. A method of claim 10 wherein the human is between 50 and 70 years of age.

17. A method of claim 10 wherein the daily administration is between one month and six months.

18. A method of claim 10 wherein the daily administration exceeds one month.

* * * * *

UNITED STATES PATENT AND TRADEMARK OFFICE
CERTIFICATE OF CORRECTION

PATENT NO : 5,407.927

DATED : April 18, 1995

INVENTOR(S) : Arlene J. Morales, et. al.

It is certified that error appears in the above-identified patent and that said Letters Patent is hereby corrected as shown below:

Title page, item [73], Assignee: should read--Research Development Foundation--.

Signed and Sealed this

First Day of August, 1995

Attest:

BRUCE LEHMAN

Attesting Officer

Commissioner of Patents and Trademarks